US00PP36141P2

(12) United States Plant Patent
van Dijk

(10) Patent No.: US PP36,141 P2
(45) Date of Patent: Sep. 24, 2024

(54) ***HYDRANGEA* PLANT NAMED 'HIISLA51'**

(50) Latin Name: *Hydrangea macrophylla*
Varietal Denomination: HIISLA51

(71) Applicant: Roy Robin van Dijk, De Lier (NL)

(72) Inventor: Roy Robin van Dijk, De Lier (NL)

(73) Assignee: HI BREEDING B.V., De Lier (NL)

( * ) Notice: Subject to any disclaimer, the term of this patent is extended or adjusted under 35 U.S.C. 154(b) by 0 days.

(21) Appl. No.: 18/534,608

(22) Filed: Dec. 9, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP16,441 P2 * 4/2006 Arts ..... A01H 6/48 Plt./250
PP26,658 P2 * 4/2016 Meinl ..... A01H 5/02 Plt./250

OTHER PUBLICATIONS

Hydrangea Breeders Association 2020 Catalogus, retrieved on Apr. 23, 2024 at https://www.hydrangeabreeders.nl/wp-content/uploads/2021/01/2020-Catalogus-HBA-potplanten-paniculata.pdf, 16 pp. (Year: 2020).*

* cited by examiner

*Primary Examiner* — June Hwu
(74) *Attorney, Agent, or Firm* — C. Anne Whealy

(57) ABSTRACT

A new and distinct cultivar of *Hydrangea* plant named 'HIISLA51', characterized by its upright and broadly spreading plant habit; moderately vigorous and moderate growth rate; freely branching habit; strong and sturdy stems; dark green-colored leaves; freely flowering habit; large and dense mophead inflorescences with purplish pink-colored sterile flowers; and good post-production longevity.

2 Drawing Sheets

Figure 1:
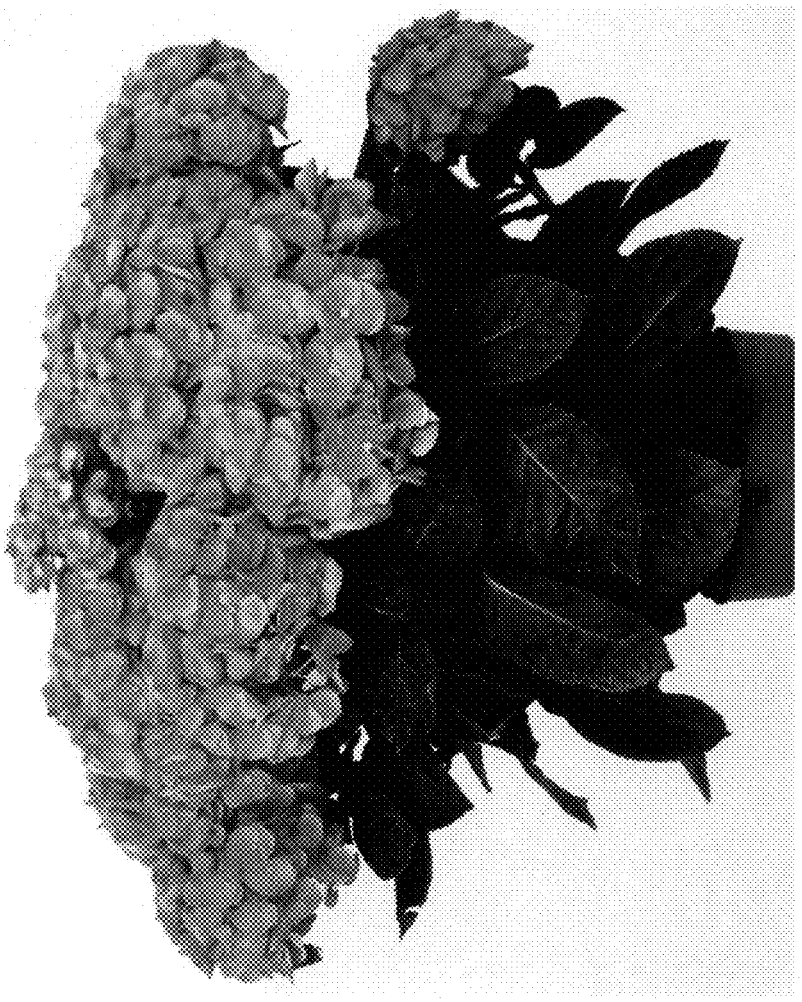

Botanical designation: *Hydrangea macrophylla.*
Cultivar denomination: 'HIISLA51'.

STATEMENT REGARDING PRIOR DISCLOSURES BY INVENTOR/APPLICANT & ASSIGNEE

The Inventor/Applicant and Assignee assert that no sales, offers for sale or public distribution of the instant plant occurred more than one year prior to the effective filing date of this application.

Any information about the claimed plant would have been obtained from a direct or indirect disclosure from the Inventor/Applicant and/or Assignee. Inventor/Applicant and Assignee claim a prior art exception under 35 U.S.C. 102 (b)(1) for disclosures and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HIISLA51'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination in April, 2017 of a proprietary selection of *Hydrangea macrophylla* identified as code number 1562, not patented, as the female, or seed, parent with a proprietary selection of *Hydrangea macrophylla* identified as code number 1793, not patented, as the male, or pollen, parent. The new *Hydrangea* plant was discovered and selected as a single flowering plant from within the progeny of the stated cross-pollination in a controlled greenhouse environment in De Lier, The Netherlands in April, 2019.

Asexual reproduction of the new *Hydrangea* plant by terminal vegetative cuttings since July, 2019 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HIISLA51'. These characteristics in combination distinguish 'HIISLA51' as a new and distinct *Hydrangea* plant:

1. Upright and broadly spreading plant habit.
2. Moderately vigorous and moderate growth rate.
3. Freely branching habit.
4. Strong and sturdy stems.
5. Dark green-colored leaves.
6. Freely flowering habit.
7. Large and dense mophead inflorescences with purplish pink-colored sterile flowers.
8. Good post-production longevity.

Plants of the new *Hydrangea* can be compared to plants of the female parent selection. Plants of the new *Hydrangea* differ primarily from plants of the female parent selection in the following characteristics:

1. Plants of the new *Hydrangea* have sturdier stems than plants of the female parent selection.
2. Sterile flowers of plants of the new *Hydrangea* are lighter purplish pink in color than sterile flowers of plants of the female parent selection.

Plants of the new *Hydrangea* can be compared to plants of the male parent selection. Plants of the new *Hydrangea* differ primarily from plants of the male parent selection in the following characteristics:

1. Plants of the new *Hydrangea* are more vigorous than plants of the male parent selection.
2. Sterile flowers of plants of the new *Hydrangea* are darker purplish pink in color than sterile flowers of plants of the male parent selection.

Plants of the new *Hydrangea* can be compared to plants of *Hydrangea macrophylla* 'HBA 202911' trade name for '200749077' (U.S. Plant Pat. No. 16,441). In side-by-side comparisons, plants of the new *Hydrangea* differ primarily from plants of 'HBA 202911' in stem strength as stems of plants of the new *Hydrangea* are sturdier than stems of plants of 'HBA 202911'. In addition, sterile flowers of plants of the new *Hydrangea* are lighter purplish pink in color than sterile flowers of plants of 'HBA 202911'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HIISLA51' grown in a container.

Figure 2:
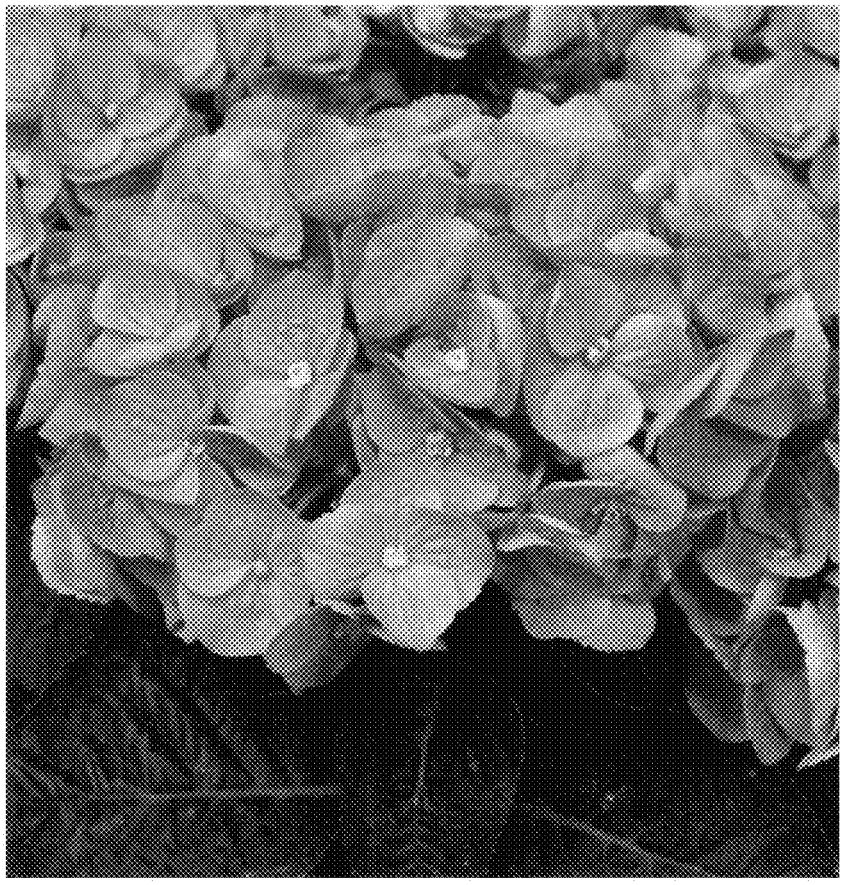

The photograph on the second sheet (FIG. 2) is a close-up view of a typical flowering plant of 'HIISLA51'.

DETAILED BOTANICAL DESCRIPTION

Plants used in the aforementioned photographs and in the following description were grown during the early summer in 13-cm containers in a glass-covered greenhouse in De Lier, The Netherlands and under cultural practices typical of commercial *Hydrangea* production. During the production of the plants, day temperatures ranged from 20C to 35C, night temperatures ranged from 10C to 22C and light levels averaged 4,000 lux. Plants of the new *Hydrangea* were pinched one time and were 18 months old when the photographs and description were taken. In the following description, color references are made to The Royal Horticultural Society Colour Chart, 2015 Edition, except where general terms of ordinary dictionary significance are used. Plants of the new *Hydrangea* can be treated with aluminum sulfate to "blue" the flower color.

Botanical description: *Hydrangea macrophylla* 'HIISLA51'.

Parentage:

*Female, or seed, patent.*—Proprietary selection of *Hydrangea macrophylla* identified as code number 1562, not patented.

*Male, or pollen, patent.*—Proprietary selection of *Hydrangea macrophylla* identified as code number 1793, not patented.

Propagation:

*Type cutting.*—By vegetative terminal cuttings.

*Time to initiate roots, summer.*—About twelve days at temperatures about 22C.

*Time to initiate roots, winter.*—About 14 days at temperatures about 20C.

*Time to produce a rooted young plant, summer.*—About 28 days at temperatures about 22C.

*Time to produce a rooted young plant, winter.*—About 30 days at temperatures about 19C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright, broadly outwardly spreading and mounding plant habit; flattened globular to broadly inverted triangular in overall shape; strong and sturdy stems; moderately vigorous growth habit and moderate growth rate; about six months from propagation are required to produce small finished flowering plants.

*Plant height.*—About 28.3 cm.

*Plant diameter or area of spread.*—About 36 cm.

Lateral branch description:

*Branching habit.*—Freely branching habit with about ten lateral branches per plant; pinching enhances lateral branch development.

*Length.*—About 16.9 cm.

*Diameter.*—About 7 mm.

*Internode length.*—About 5 cm.

*Strength.*—Strong, sturdy.

*Aspect.*—About 40 to 90 degrees from vertical.

*Texture.*—Smooth, glabrous; becoming woody with development.

*Color, developing.*—Close to 144A; at the nodes, strongly tinged with close to N186B.

*Color, fully developed.*—Close to 144B; distally at the nodes, strongly tinged with close to N186B; when woody, close to 199A to 199B and N199C.

*Lenticels.*—Density: Moderate. Length: About 1 mm. Diameter: About 0.5 mm. Color: Close to N186A and N186B.

Leaf description:

*Arrangement.*—Opposite, simple.

*Length.*—About 10.8 cm.

*Width.*—About 8.1 cm.

*Shape.*—Broadly obovate to short and broadly oblong.

*Apex.*—Apiculate.

*Base.*—Short attenuate to truncate.

*Margin.*—Dentate-crenate.

*Texture, upper and lower surfaces.*—Slightly rugose, glabrous.

*Venation pattern.*—Pinnate.

*Color.*—Developing leaves, upper surface: Close to NN137A. Developing leaves, lower surface: Close to 146A. Fully developed leaves, upper surface: Close to a blend of NN137A and 147A; venation, close to 145B. Fully developed leaves, lower surface: Close to 147B; venation, close to 146D.

*Petioles.*—Length: About 2.7 cm. Diameter: About 3.5 mm to 4 mm. Texture and luster, upper and lower surfaces: Smooth, glabrous; slightly glossy. Color, upper surface: Close to 145B with margins, close to 144A. Color, lower surface: Close to 146D; midvein, close to 147B.

Flower description:

*Flower type and habit.*—Showy rotate sterile flowers and small, inconspicuous rotate fertile flowers arranged on mophead-type terminal panicles; panicles flattened globular in shape; sterile flowers face upright to outwardly, fertile flowers face mostly upright.

*Fragrance.*—None detected.

*Natural flowering season.*—In the garden, plants flower continuously from the late spring to late summer in The Netherlands; flower dormancy can be broken with a cold storage treatment.

*Flower longevity.*—Good postproduction longevity; sterile flowers maintain good substance for about six weeks on the plant, sterile flowers persistent; fertile flowers last for a few days on the plant, fertile flowers not persistent.

*Quantity of flowers.*—Freely flowering habit; about 190 sterile flowers per panicle and about 70 fertile flowers per panicle.

*Panicle height.*—About 10.3 cm.

*Panicle diameter.*—About 15.8 cm.

*Panicle peduncles.*—Length: About 3.9 cm. Diameter: About 3.5 mm. Strength: Strong. Aspect: Primary peduncles, mostly erect; lateral peduncles, about 40 degrees from primary peduncle axis. Texture: Moderately pubescent. Color: Close to 144A; at the nodes, tinged with close to N186C.

*Sterile flower buds.*—Length: About 9 mm. Diameter: About 1.2 cm. Shape: Cup-shaped. Color: Close to a blend of 149C and 150C and towards the apex, close to 182B; when "blued", close to N88D and towards the base, close to 84C.

*Fertile flower buds.*—Length: About 3.5 mm. Diameter: About 3.5 mm. Shape: Globular. Color: Close to 182D; when "blued", close to 98A.

*Sterile flower diameter.*—About 2.4 cm to 3.5 cm.

*Sterile flower depth (height).*—About 1.4 cm.

*Fertile flower diameter.*—About 1 cm.

*Fertile flower depth (height).*—About 5 mm.

*Petals, sterile flowers.*—Quantity and arrangement: Four, in a single whorl. Length: About 3.5 mm. Width: About 2 mm. Shape: Ovate, moderately concave. Apex: Acute. Base: Cuneate. Margin: Entire. Texture and luster, upper and lower surfaces: Smooth, glabrous; matte. Color: When opening and fully opened, upper surface: Close to 91A and at the margins, close to 92D; when "blued", close to 116B with margins, close to 92D; color does not change with subsequent development. When opening and fully opened, lower surface: Close to N80C and at the margins, close to 92D; when "blued", close to 102D with margins, close to 92D; color does not change with subsequent development.

*Petals, fertile flowers.*—Quantity and arrangement: About five in a single whorl. Length: About 5 mm. Width: About 3 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to N79D; when "blued", close to 102D; color does not change with subsequent development. When opening and fully opened, lower surface: Close to N77B; when "blued", close to 102C to 102D; color does not change with subsequent development.

*Sepals, sterile flowers.*—Quantity and arrangement: Typically four or five, or rarely six, in a single whorl; moderately to strongly imbricate. Length: About 1.8 cm. Width: About 2 cm. Shape: Reniform to close to broadly deltoid; slightly to moderately concave. Apex: Broadly and bluntly acute to broadly acute. Base: Cuneate to shallowly truncate. Margin: Proximally, entire, and distally, crenate. Texture and luster, upper and lower surfaces: Rugose, glabrous; matte. Color: When opening, upper surface: Close to 73B and towards the apex, close to a blend of 73A and 73B; when "blued", close to 102D and towards the apex, close to 100C. When opening, lower surface: Close to 73B and towards the apex, close to a blend of 73A and 73B; when "blued", close to 98C. Fully opened, upper surface: Close to 73B; when "blued", close to 96D and towards the margins and apex, close to 97A; with subsequent development, color becoming closer to 146D and when "blued", closer to N88C and eventually, close to 146B. Fully opened, lower surface: Close to 68C; when "blued", close to 97A; with subsequent development, color becoming closer to 146D and when "blued", closer to 91A and N87D and eventually, close to 146C.

*Sepals, fertile flowers.*—Quantity and arrangement: Five in a single whorl. Length: About 1.5 mm. Width: About 1.5 mm. Shape: Broadly ovate to broadly elliptic. Apex: Acute. Base: Cuneate. Margin: Entire. Texture and luster, upper and lower surfaces: Smooth, glabrous; matte. Color: When opening and fully opened, upper surface: Close to 146D with margins, close to 63D; when "blued", close to 116D; color does not change with subsequent development. When opening and fully opened, lower surface: Close to 146D and apices, close to 147A; when "blued", close to 116D; color does not change with subsequent development.

*Pedicels, sterile flowers.*—Length: About 1.4 cm. Diameter: About 1.75 mm. Strength: Moderately strong. Aspect: About 60 degrees from main peduncle axis. Texture and luster: Moderately pubescent; matte. Color: Close to 59D; when "blued", close to 98B.

*Pedicels, fertile flowers.*—Length: About 3 mm. Diameter: About 1 mm. Strength: Moderately strong. Aspect: About 5 degrees from vertical. Texture and luster: Sparsely pubescent; matte. Color: Close to 84C; when "blued", close to 116D.

*Reproductive organs, sterile flowers.*—Stamens: Quantity per flower: About eight. Filament length: About 2 mm. Filament color: Close to N155B. Anther length: About 1 mm. Anther shape: Broadly oblong. Anther color: Close to 155D; when "blued", close to 108D. Pollen amount: Moderate. Pollen color: Close to 156A. Pistils: Pistil quantity per flower: About two or three. Pistil length: About 1.5 mm. Stigma shape: Club-shaped. Stigma color: Close to N155A. Style length: About 1 mm. Style color: Close to N155A. Ovary color: Close to 157D.

*Reproductive organs, fertile flowers.*—Stamens: Quantity per flower: About ten. Filament length: About 3 mm. Filament color: Close to N155B. Anther length: About 1 mm. Anther shape: Broadly oblong. Anther color: Close to 155D; when "blued", close to 108D. Pollen amount: Moderate. Pollen color: Close to 156A. Pistils: Pistil quantity per flower: About two or three. Pistil length: About 1.5 mm. Stigma shape: Club-shaped. Stigma color: Close to N155A. Style length: About 1 mm. Style color: Close to N155A. Ovary color: Close to 157D.

*Seeds.*—To date, seed development has not been observed on plants of the new *Hydrangea.*

Pathogen & pest resistance: Plants of the new *Hydrangea* have been observed to be tolerant to *Botrytis* (*Botrytis cinerea*). To date, plants of the new *Hydrangea* have not been observed to be resistant to pests and other pathogens common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HIISLA51' herein as illustrated and described.

* * * * *